United States Patent
Chuang et al.

(10) Patent No.: US 11,294,032 B2
(45) Date of Patent: Apr. 5, 2022

(54) DOPPLER RADAR SENSOR WITH POWER DETECTOR

(71) Applicants: Sil Radar Technology Inc., Kaohsiung (TW); National Cheng Kung University, Tainan (TW); NCKU Research and Development Foundation, Tainan (TW)

(72) Inventors: Huey-Ru Chuang, Tainan (TW); Chien-Chang Chou, Tainan (TW); Wen-Chian Lai, Tainan (TW)

(73) Assignees: Sil Radar Technology Inc., Kaohsiung (TW); National Cheng Kung University, Tainan (TW); NCKU Research and Devvelopment Foundation, Tainan (TW)

( * ) Notice: Subject to any disclaimer, the term of this patent is extended or adjusted under 35 U.S.C. 154(b) by 470 days.

(21) Appl. No.: 16/446,801

(22) Filed: Jun. 20, 2019

(65) Prior Publication Data
US 2020/0025876 A1 Jan. 23, 2020

(30) Foreign Application Priority Data
Jul. 17, 2018 (TW) ................. 107124709

(51) Int. Cl.
*G01S 7/41* (2006.01)
*G01S 7/03* (2006.01)
(Continued)

(52) U.S. Cl.
CPC ............ *G01S 7/414* (2013.01); *A61B 5/0205* (2013.01); *A61B 5/1102* (2013.01); *A61B 5/113* (2013.01); *G01S 7/03* (2013.01); *G01S 7/354* (2013.01)

(58) Field of Classification Search
CPC . G01S 7/414; G01S 7/03; G01S 7/354; G01S 7/038; G01S 7/415; G01S 13/89;
(Continued)

(56) References Cited

U.S. PATENT DOCUMENTS

| 5,264,855 A | 11/1993 | Lammers et al. |
| 6,693,971 B1 * | 2/2004 | Kowalski ............... H04B 15/00 375/285 |

(Continued)

FOREIGN PATENT DOCUMENTS

TW    I609192 B    12/2017

OTHER PUBLICATIONS

Kuo, et al., A 60-GHz CMOS Direct-Conversion Doppler Radar RF Sensor with Clutter Canceller for Single-Antenna Noncontact Human Vital-Signs Detection, 2015 IEEE Radio Frequency Integrated Circuits Symposium, Mar. 2015. (Year: 2015).*

(Continued)

*Primary Examiner* — Donald HB Braswell
(74) *Attorney, Agent, or Firm* — Demian K. Jackson; Jackson IPG PLLC

(57) ABSTRACT

A Doppler radar sensor with a power detector is disclosed. In the Doppler radar sensor, a power detector is provided to detect the power level of a received transmission signal, and a leakage and clutter canceler is provided to generate a cancellation signal according to the power level of the received transmission signal. The cancellation signal is used to cancel leakage and clutter in the received transmission signal such that object displacement in the received transmission signal can be identified.

11 Claims, 3 Drawing Sheets

(51) Int. Cl.
　　　*G01S 7/35*　　　(2006.01)
　　　*A61B 5/113*　　(2006.01)
　　　*A61B 5/11*　　　(2006.01)
　　　*A61B 5/0205*　(2006.01)

(58) Field of Classification Search
　　　CPC ...... G01S 13/522; G01S 13/536; G01S 13/52;
　　　　　　　G01S 13/88; A61B 5/0205; A61B 5/1102;
　　　　　　　　A61B 5/113; A61B 5/0507; A61B 5/024;
　　　　　　　　　　A61B 5/0816; A61B 5/11
　　　See application file for complete search history.

(56)　　　　　　　　References Cited

U.S. PATENT DOCUMENTS

| | | | |
|---|---|---|---|
| 6,733,455 | B2 | 5/2004 | Mo et al. |
| 2006/0240769 | A1* | 10/2006 | Proctor Jr ............ H04B 7/15585 |
| | | | 455/24 |
| 2018/0113193 | A1* | 4/2018 | Huemer ................. G01S 13/343 |
| 2019/0170857 | A1* | 6/2019 | Nakajima .............. G01S 13/931 |

OTHER PUBLICATIONS

Taiwanese Office Action dated Mar. 12, 2019 for Taiwanese Patent Application No. 107124709, 5 pages.
Chien-Chang Chou et al., 60-GHz CMOS Doppler Radar Sensor With Integrated V-Band Power Detector for Clutter Monitoring and Automatic Clutter-Cancellation in Noncontact Vital-Signs Sensing, IEEE Transactions on Microwave Theory and Techniques, Dec. 11, 2017.

\* cited by examiner

DOPPLER RADAR SENSOR WITH POWER DETECTOR

FIELD OF THE INVENTION

This invention generally relates to a Doppler radar sensor, and more particularly to a Doppler radar sensor with power detector.

BACKGROUND OF THE INVENTION

Vital signs are usually measured by contact type measurement devices. The subject may feel uncomfortable during measurement due to the measurement devices have to contact the subject's skin for a long time and the subject's moving range is limited by the wires connected to the measurement device. Consequently, non-contact type measurement devices are better than contact type ones for long-term continuous vital signs monitoring. The conventional Doppler radar sensor is applied to detect object's displacement because of the Doppler Effect. When the wireless signals are transmitted from the Doppler radar sensor to the object, the object's displacement relative to the Doppler radar induces the Doppler shifts of the wireless signals such that the reflected RF signals from the object contains the phase-demodulated component of the object's displacement. After receiving and demodulating the reflected RF signals by the Doppler radar, the displacement signals of the object can be obtain. Nevertheless, the Doppler radar, radiating the wireless signals divergently, not only receives the reflected RF signals from the object hut also receives clutter from background, and may generate leakage signals. Identifying the displacement signals of the object from the reflected RE signals is difficult due to the clutter and leakage.

SUMMARY

The object of the present invention is to utilize a power detector to detect the power of leakage from Doppler radar sensor and clutter reflected from background, and utilize a cancellation signal generated by a leakage and clutter canceler to cancel the leakage and clutter. Accordingly, the leakage and clutter can be cancelled automatically by the cancellation signal from the leakage and clutter canceler to obtain the object displacement signal precisely.

A Doppler radar sensor of the present invention includes a radar, a power detector and a leakage and clutter canceler. The radar is configured to radiate a wireless signal to an object and receive a reflected signal from the object and a clutter from a background where the object is placed, A received transmission signal is formed from the reflected signal, the clutter and a leakage signal of the radar. The power detector is coupled to the radar and configured to detect a power level of the received transmission signal and output a detection signal according to the power level of the received transmission signal. The leakage and clutter canceler is coupled to the power detector and configured to receive the detection signal and generate a cancellation signal to the radar according to the detection signal. The cancellation signal is configured to cancel the leakage signal and the clutter in the received transmission signal.

In the present invention, the power detector is provided to detect the power level of the received transmission signal and the leakage and clutter canceler is provided to generate the cancellation signal according to the power level detected by the power detector. Hence, the leakage signal and clutter in the received transmission signal can be cancelled automatically and the displacement signal involved in the received transmission signal can be identified.

DETAILED DESCRIPTION OF THE INVENTION

Figure 1:
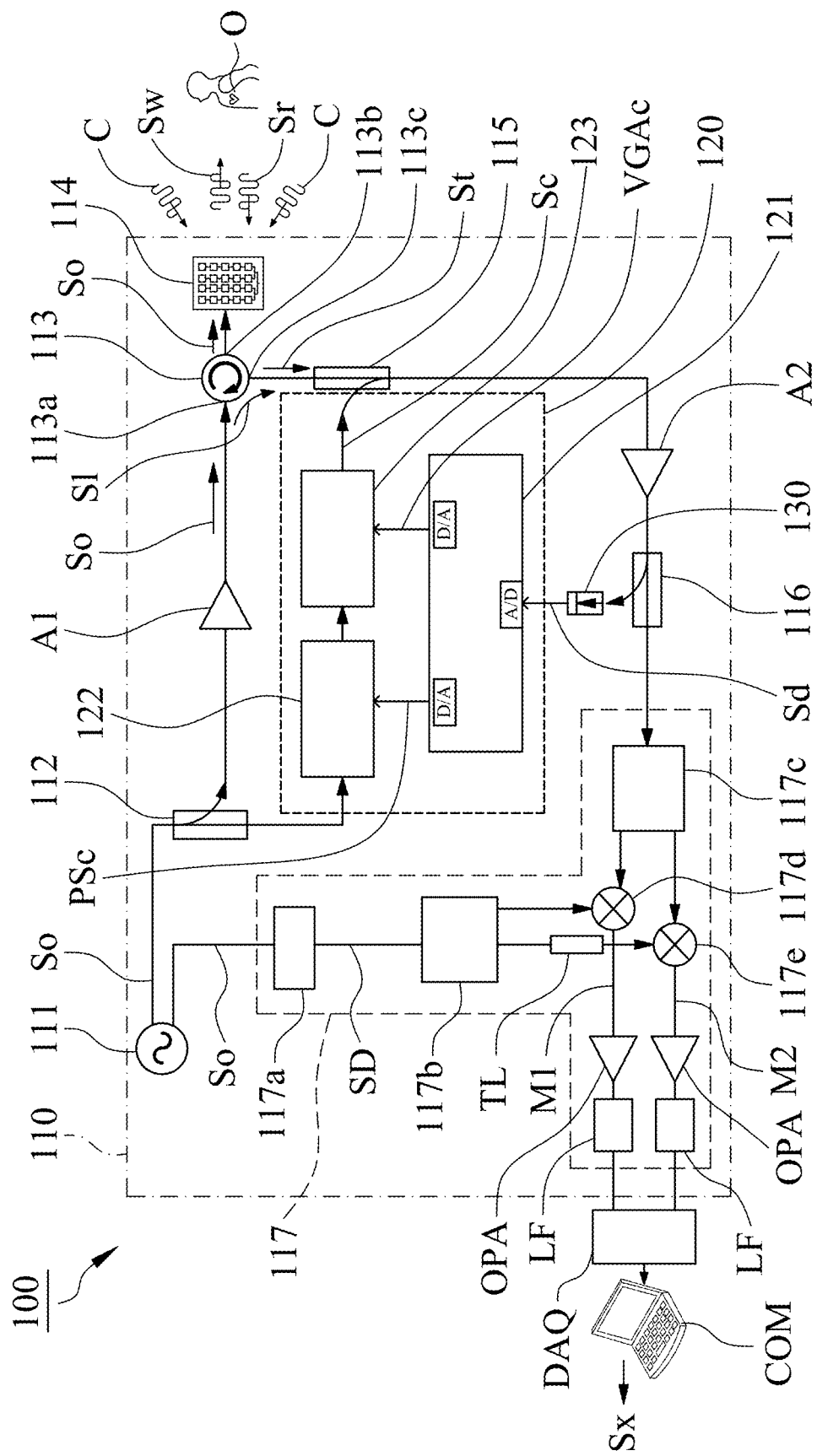
FIG. 1 is a functional block diagram illustrating a Doppler radar sensor with power detector in accordance with one embodiment of the present invention.

FIG. 1 is a functional block diagram of a Doppler radar sensor 100 in accordance with one embodiment of the present invention. The Doppler radar sensor 100 includes a radar 110, a leakage and clutter canceler 120 and a power detector 130. And preferably, the radar 110, the leakage and clutter canceler 120 and the power detector 130 are integrated into an integrated circuit.

The radar 110 may be continuous-wave (CW) radar or pulse radar with signal antenna or multiple antennas. In this embodiment, a simpler architecture, CW radar with single antenna, is utilized to detect object's displacements in order to reduce the layout area of the Doppler radar sensor 100. The radar 110 includes a signal generator 111, a first coupler 112, a circulator 113, an antenna 114, a second coupler 115, a third coupler 116 and a demodulator 117. The signal generator 111 is configured to generate an oscillation signal So, and the oscillation frequency range of the oscillation signal So is from 40 to 80 GHz. In this embodiment, the oscillation frequency of the oscillation signal So is 60 GHz. The first coupler 112 is electrically connected to the signal generator 111 and configured to receive and split the oscillation signal So into two paths. A first amplifier A1 is electrically connected to the first coupler 112 and configured to amplify the oscillation signal So of one path. The circulator 113 is electrically connected to the first amplifier A1 and configured to receive the amplified oscillation signal So from the first amplifier A1.

The circulator 113 has a first port 113a, a second port 113b and a third port 113c. Ideally, the signal into the circulator 113 via the first port 113a is only output from the second port 113b, the signal into the circulator 113 via the second port 113b is only output from the third port 113c and the signal. 1.5 into the circulator 113 via the third port 113c is only output from the first port 113a. However, the oscillation signal So into the non-ideal circulator 113 via the first port 113a may leak to the third port 113c as a leakage signal S1. For this reason, the signal output from the third port 113c is not only the signal into the second port 113b.

With reference to FIG. 1, in this embodiment, the oscillation signal So amplified by the first amplifier A1 is input to the circulator 113 via the first port 113a and output from the second port 113b, then the oscillation signal So is transmitted from the second port 113b to the antenna 114. The antenna 114 is configured to radiate the oscillation signal So as a wireless signal Sw toward an object O and receive a reflected signal Sr from the object and a clutter C from an environment where the object O is placed. A received transmission signal St is formed from the reflected signal Sr and the clutter C received by the antenna 114 of the radar 110. The displacements of the object O relative to the antenna 114 may cause the Doppler shifts in the wireless signal Sw, consequently, the reflected signal Sr may include the phase modulation components of the displacements of the object O. The received transmission signal St is input to the circulator 113 via the second port 113b and output from the circulator 113 via the third port 113c. However, the amplified oscillation signal So may leak the leakage signal S1 to the third port 113c when it is transmitted to the first port 113a, and the leakage signal S1 may mix with the received transmission signal St such that the phase modulation components of the displacements of the object O in the received transmission signal S1 can't be identified directly.

The displacements of the object O relative to the antenna 114 may be non-organism movements or tiny vibrations caused by organism vital signs. The detection object of the present invention is not limited to human of the embodiment.

With reference to FIG. 1, the leakage and clutter canceler 120 is electrically connected to the first coupler 112 and configured to receive the oscillation signal So of the other path. The leakage and clutter canceler 120 includes a microprocessor control unit (MCU) 121, an adjustable phase shifter 122 and a variable gain amplifier 123. In this embodiment, the oscillation signal So from the first coupler 112 is transmitted to the adjustable phase shifter 122 to adjust the phase and then transmitted to the variable gain amplifier 123 to adjust the amplitude so as to form a cancellation signal Sc. The MCU 121 is electrically connected to the adjustable phase shifter 122 and the varied gain amplifier 123. The MCU 121 is configured to output a control signal PSc to the adjustable phase shifter 122 to control the phase shift of the adjustable phase shifter 122, and configured to output a control signal VGA to the varied gain amplifier 123 to control the gain of the varied gain amplifier 123.

With reference to FIG. 1, the second coupler 115 is electrically connected to the third port 113c of the circulator 113 and the leakage and clutter canceler 120. The second coupler 115 is configured to receive and couple the received transmission signal St and the cancellation signal Sc. The phase and the amplitude of the cancellation signal Sc are adjusted by the adjustable phase shifter 122 and the varied gain amplifier 123, respectively, such that the cancellation signal Sc is able to cancel the clutter C and the leakage signal S1 in the received transmission signal St to identify a displacement signal Sx involved in the received transmission signal St.

With reference to FIG. 1, a second amplifier A2 is electrically connected to the second coupler 115 and configured to amplify the received transmission signal St from the second coupler 115. The third coupler 116 is coupled to the second coupler 115 via the second amplifier A2 and configured to receive and split the amplified received transmission signal St into two paths. The power detector 130 is electrically connected to the third coupler 116 and configured to receive the received transmission signal St of one path from the third coupler 116.

With reference to FIG. 1, the power detector 130 is configured to detect a power level of the received transmission signal St and output a detection signal Sd according to the power level of the received transmission signal St. The MCU 121 of the leakage and clutter canceler 120 is electrically connected to the power detector 130 for receiving the detection signal Sd. Based on the detection signal Sc, the MCU 121 can output the control signal PSc to control the phase shift of the adjustable phase shifter 122 and output the control signal VGAc to control the gain of the varied gain amplifier 123.

In this embodiment, the MCU 121 provides the entire control ranges of the control signals PSc and VGAc to the adjustable phase shifter 122 and the varied gain amplifier 123, respectively, and utilizes the power level of the received transmission signal St from the detection signal Sd to optimize the control signals PSc and VGAc. The clutter C and the leakage signal S1 in the received transmission signal St may increase the power level of the received transmission signal St, and the cancellation level of the clutter C and the leakage signal S1 by the cancellation signal Sc of the leakage and clutter canceler 120 may be different when the MCU 121 uses different control signals PSc and VGAc to adjust the adjustable phase shifter 122 and the varied gain amplified 123. Consequently, the clutter C and the leakage signal S1 in the received transmission signal St are cancelled by the cancellation signal Sc as much as possible when the power level of the received transmission signal St showing in the detection signal Sd is minimum. That is, the phase shift from the adjustable phase shifter 122 and the gain from the varied gain amplifier 123 are optimal.

The clutter C and the leakage signal S1 in the received transmission signal St are cancelled automatically by the power detecting of the power detector 130 and the cancellation signal Sc generated by the leakage and clutter canceler 120 according to the detection signal Sd. As a result, the displacement signal Sic in the received transmission signal St can be identified in subsequent procedures.

Figure 2:
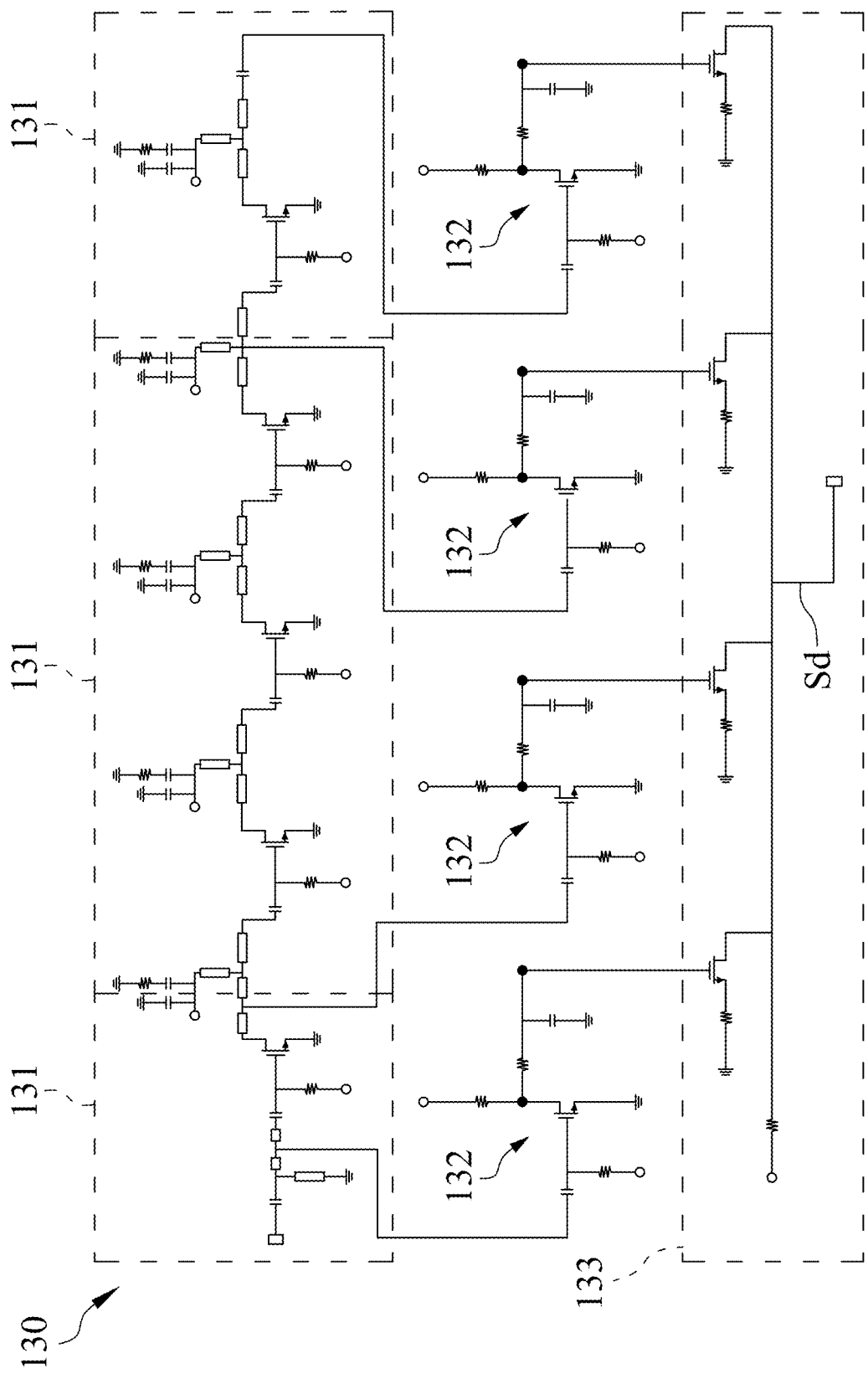
FIG. 2 is a circuit diagram illustrating a power detector in accordance with one embodiment of the present invention.

FIG. 2 is a circuit diagram of the power detector 130 which is a successive detection logarithmic amplifier (SDLA). The operating frequency range of the Doppler radar sensor 100 is from 40 to 80 GHz in this embodiment, and limited amplifiers of gain stages in the power detector 130 are preferably replaced by common-source amplifiers in order to decrease the power loss of the power detector 130 while operating in high frequency range. In this embodiment, the power detector 130 includes a plurality of gain stages 131, a plurality of rectifiers 132 and a voltage summation unit 133. The gain stages 131 are connected in cascade with each other, Each of the gain stages 131 is composed of a single or multiple common-source amplifiers and configured to output a voltage. The rectifiers 132 are each electrically connected to one of the gain stages 131 to convert the voltage of the gain stage 131 to an output voltage. The voltage summation unit 133 is electrically connected to the rectifiers 132 and configured to receive and sum the output voltages to generate a summed voltage. The summed voltage is the detection signal Sd, and the potential level of the detection signal Sd is proportional to the power level of the received transmission signal St.

Referring to FIG. 1 again, the leakage and clutter canceler 120 is provided to adjust the phase and amplitude of the cancellation signal Sc based on the detection signal Sd and cancel the clutter C and the leakage signal S1 in the received transmission signal St by using the cancellation signal Sc. Consequently, the displacement signal Sx in the received transmission signal St is able to be identified. The demodulator 117 of the radar 110 is electrically connected to the signal generator 111 and the third coupler 116 and configured to receive and demodulate the oscillation signal So and the received transmission signal St of the other path to obtain the displacement signal Sx of the object O.

With reference to FIG. 1, the demodulator 117 in this embodiment includes a frequency divider 117a, a first power divider 117b, a second power divider 117c, a first subharmonic mixer 117d and a second subharmonic mixer 117e, The frequency divider 117a is electrically connected to the signal generator 111 for receiving the oscillation signal So and configured to divide the oscillation signal So by 2 and output a divided signal SD. The first power divider 117b is electrically connected to the frequency divider 117a and configured to receive and divide the divided signal SD into two paths. The divided signal SD of one path is transmitted to the first subharmonic mixer 117d, and the divided signal SD of the other path is transmitted to the second subharmonic mixer 117e through a transmission line IL. The second power divider 117c is electrically connected to the third coupler 116 to receive the received transmission signal St, And the second power divider 117c is provided to divide the received transmission signal St into two paths, the received transmission signal St of two paths are transmitted to the first subharmonic mixer 117d and the second subharmonic mixer 117e, respectively. The first subharmonic mixer 117d is configured to mix the divided signal SD and the received transmission signal St and output a first mixing signal M1. The second subharmonic mixer 117e is configured to mix the phase-shifted divided signal SD and the received transmission signal St and output a second mixing signal M2. The first mixing signal M1 is transmitted to a computing device COM via an amplifier OPA, a low-pass filter LF and a data acquisition device DAQ, and the second mixing signal M2 is transmitted to the computing device COM via another amplifier OPA, another low-pass filter LF and the data acquisition device DAQ. The displacement signal Sx is obtained from the first and second mixing signal M1 and M2 transmitted to the computing device COM.

Figure 3:
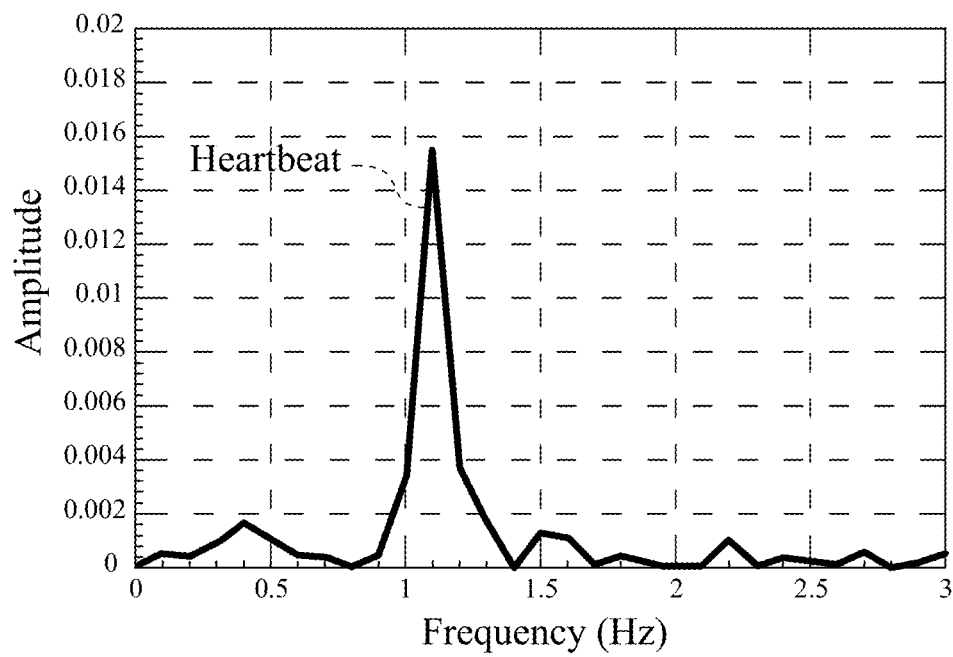
FIG. 3 is a measurement result showing displacement signal of a human subject who is holding breath by using the Doppler radar sensor with power detector in accordance with one embodiment of the present invention.
Figure 4:
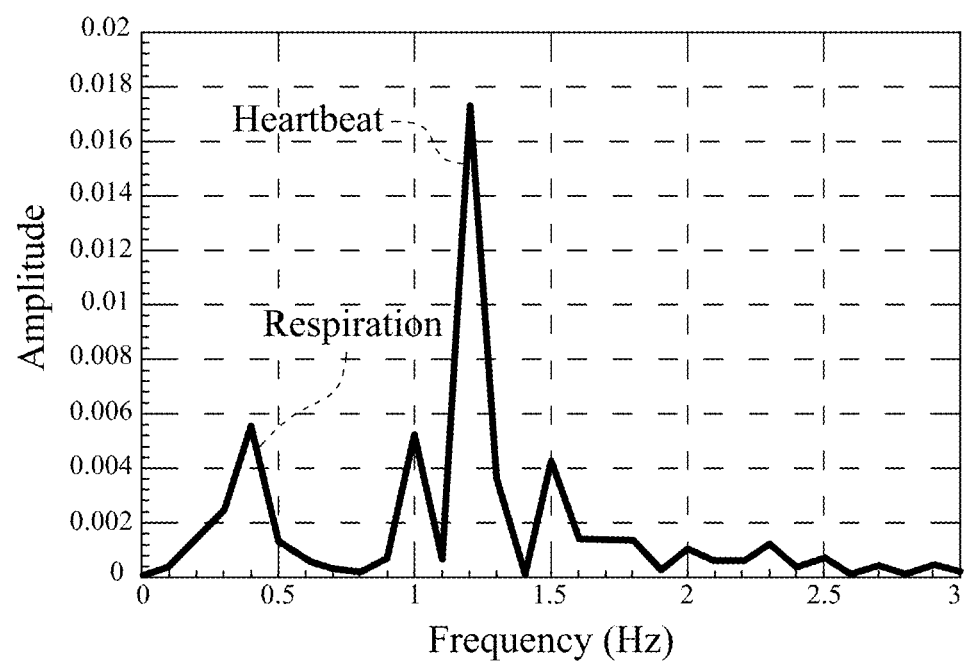
FIG. 4 is a measurement result showing displacement signal of a human subject who is breathing normally by using the Doppler radar sensor with power detector in accordance with one embodiment of the present invention.

FIGS. 3 and 4 are the measurement results of displacement signals of a human subject by using the Doppler radar sensor 100 of the present invention. The vital signs of the human subject cause displacements so that the detected displacement signals represent the vital signs of the human subject. When the human subject is holding breathing, as shown in FIG. 3, only the displacement caused by heartbeat is measured. The displacements caused by heartbeat and respiration can be measured as shown in FIG. 4 while the human subject is breathing normally. Thus, it can be seen that the Doppler radar sensor 100 of the present invention can cancel the clutter C from the background and the leakage signal S1 from the circulator 113 as much as possible to measure the vital signs of the human subject precisely.

In the present invention, the power detector 130 is provided to detect the power level of the received transmission signal St and the leakage and clutter canceler 120 is provided to generate the cancellation signal Sc according to the power level detected by the power detector 130. Hence, the clutter C and the leakage signal S1 in the received transmission signal St can be cancelled automatically, and the displacement signal involved in the received transmission signal St can be identified.

While this invention has been particularly illustrated and described in detail with respect to the preferred embodiments thereof, it will be clearly understood by those skilled in the art that is not limited to the specific features shown and described and various modified and changed in form and details may be made without departing from the spirit and scope of this invention.

What is claimed is:

1. A Doppler radar sensor, comprising:
a radar configured to radiate a wireless signal to an object and receive a reflected signal from the object and a clutter from a background where the object is placed, wherein a received transmission signal is formed from the reflected signal, the clutter and a leakage signal of the radar;
a power detector coupled to the radar, the power detector is configured to detect a power level of the received transmission signal and output a detection signal according to the power level of the received transmission signal; and
a leakage and clutter canceler coupled to the power detector, the leakage and clutter canceler is configured to receive the detection signal and generate a cancellation signal to the radar according to the detection signal, wherein the cancellation signal is configured to cancel the leakage signal and the clutter in the received transmission signal.

2. The Doppler radar sensor in accordance with claim 1, wherein the leakage and clutter canceler includes a microprocessor control unit, an adjustable phase shifter and a varied gain amplifier, the microprocessor control unit is electrically connected to the power detector and configured to receive the detection signal, and the microprocessor control unit is further configured to output control signals according to the detection signal to the adjustable phase shifter and the varied gain amplifier, respectively.

3. The Doppler radar sensor in accordance with claim 2, wherein the radar includes a signal generator, a first coupler, a circulator and an antenna, the signal generator is configured to generate an oscillation signal, the first coupler is configured to receive and split the oscillation signal into two paths, the circulator is electrically connected to the first coupler and configured to receive and transmit the oscillation signal of one path to the antenna, the antenna is configured to radiate the oscillation signal as the wireless signal to the object, the leakage and clutter canceler is electrically connected to the first coupler and configured to receive the oscillation signal of the other path and adjust a phase and a amplitude of the oscillation signal to form the cancellation signal.

4. The Doppler radar sensor in accordance with claim 3, wherein the radar further includes a second coupler electrically connected to the circulator and the leakage and clutter canceler, the second coupler is configured to receive and couple the received transmission signal and the cancellation signal.

5. The Doppler radar sensor in accordance with claim 3, wherein the radar further includes a first amplifier which is electrically connected to the first coupler and configured to amplify the oscillation signal, the circulator is coupled to the first coupler via the first amplifier and configured to receive the amplified oscillation signal.

6. The Doppler radar sensor in accordance with claim 4, wherein the radar further includes a third coupler electrically connected to the second coupler, the third coupler is configured to receive and split the received transmission signal into two paths, the power detector is electrically connected to the third coupler and configured to receive the received transmission signal of one path from the third coupler.

7. The Doppler radar sensor in accordance with claim 6, wherein the radar further includes a second amplifier which is electrically connected to the second coupler and configured to amplify the received transmission signal, the third coupler is coupled to the second coupler via the second amplifier and configured to receive the amplified received transmission signal.

8. The Doppler radar sensor in accordance with claim 7, wherein the radar further includes a demodulator electrically connected to the signal generator and the third coupler, the demodulator is configured to receive and demodulate the oscillation signal and the received transmission signal of the other path to obtain a displacement signal of the object.

9. The Doppler radar sensor in accordance with claim 1, wherein the power detector includes a plurality of gain stages, a plurality of rectifiers and a voltage summation unit, the gain stages are connected in cascade with each other and each is configured to output a voltage, each of the rectifiers is electrically connected to one of the gain stages and configured to convert the voltage of the gain stage into a output voltage, the voltage summation unit is electrically connected to the rectifiers and configured receive and sum the output voltages to generate a summed voltage.

10. The Doppler radar sensor in accordance with claim 9, wherein each of the gain stages is composed of a single or multiple common-source amplifiers.

11. The Doppler radar sensor in accordance with claim 1, wherein an operating frequency range of the Doppler radar sensor is from 40 to 80 GHz.

* * * * *